United States Patent
Yun et al.

(10) Patent No.: US 11,969,520 B2
(45) Date of Patent: Apr. 30, 2024

(54) RESORPTION INORGANIC BINDER FOR MEDICAL USE AND METHOD OF PREPARING BONE SUBSTITUTE USING SAME

(71) Applicant: HUDENS BIO CO., LTD., Gwangju (KR)

(72) Inventors: Kye Lim Yun, Jeollanam-do (KR); Suk Young Kim, Gyeongsangbuk-do (KR); Joo Seong Kim, Gyeongsangbuk-do (KR); Jae Ick Han, Gwangju (KR); Hak Noh, Gyeonggi-do (KR)

(73) Assignee: HUDENS BIO CO., LTD., Gwangju (KR)

( * ) Notice: Subject to any disclaimer, the term of this patent is extended or adjusted under 35 U.S.C. 154(b) by 259 days.

(21) Appl. No.: 17/523,101

(22) Filed: Nov. 10, 2021

(65) Prior Publication Data

US 2022/0273843 A1 Sep. 1, 2022

(30) Foreign Application Priority Data

Feb. 26, 2021 (KR) .......................... 10-2021-0026924

(51) Int. Cl.
*B28B 11/22* (2006.01)
*A61L 27/12* (2006.01)

(52) U.S. Cl.
CPC .............. *A61L 27/12* (2013.01); *B28B 11/22* (2013.01); *A61L 2300/802* (2013.01); *A61L 2430/02* (2013.01)

(58) Field of Classification Search
CPC ..... B28B 11/22; A61L 27/12; A61L 2300/802
USPC ....................................................... 264/299
See application file for complete search history.

(56) References Cited

U.S. PATENT DOCUMENTS 7,517,539 B1 4/2009 Lee et al.

FOREIGN PATENT DOCUMENTS

| CN | 110251723 A | 9/2019 |
| JP | 2005-067966 A | 3/2005 |
| KR | 10-2020-0056282 A | 5/2020 |
| WO | WO 2012/089276 A1 | 7/2012 |
| WO | WO 2017/048155 A1 | 3/2017 |

OTHER PUBLICATIONS

English translation of KR20200056282 (Year: 2020).*
European Search Report for EP 21207841.4 dated May 12, 2022 from European patent office in a counterpart European patent application.

* cited by examiner

*Primary Examiner* — Jeffrey M Wollschlager
*Assistant Examiner* — Xue H Liu
(74) *Attorney, Agent, or Firm* — The PL Law Group, PLLC

(57) ABSTRACT

A method of preparing an inorganic binder for medical use according to an embodiment of the present disclosure includes preparing a starting material using a-TCP powder and phosphate powder each of which has a predetermined particle size, producing a paste having a predetermined viscosity that is suitable for formation of a molded article having a predetermined shape by homogeneously mixing the starting material, adding water or saline to the homogeneously mixed starting material, and kneading the resulting mixture, subjecting the molded article to hydration reaction, and washing and drying the molded article having undergone the hydration reaction to obtain an inorganic binder containing OCP and HA crystal phases.

14 Claims, 7 Drawing Sheets

RESORPTION INORGANIC BINDER FOR MEDICAL USE AND METHOD OF PREPARING BONE SUBSTITUTE USING SAME

CROSS REFERENCE TO RELATED APPLICATION

The present application claims priority to Korean Patent Application No. 10-2021-0026924, filed Feb. 26, 2021, the entire contents of which is incorporated herein for all purposes by this reference.

BACKGROUND

1. Field of the Invention

The present disclosure relates to a medical inorganic binder and a method of preparing a bone substitute using the same. More particularly, the present disclosure relates to a method of preparing an inorganic binder containing octacalcium phosphate (OCP) at low temperatures (for example, 100° C. or lower) by using α-tricalcium phosphate (α-TCP) as a starting material, and a method of preparing a bone substitute by adding a calcium phosphate-based material such as octacalcium phosphate, hydroxy apatite (HA), β-tricalcium phosphate (β-TCP), or dicalcium phosphate dihydrate (DCPD) to the prepared inorganic binder serving as a starting material.

2. Description of the Related Art

The human body is composed of the skin, soft tissues forming various organs, and hard tissues forming various bones and teeth. The bones that function to support the body and protect various important organs are composed of calcium phosphate-based minerals (about 70%), which are comprised of calcium and phosphorus, and organic substances (30%), which are comprised of collagen and non-collagen. That is, the bones are composite materials.

On the other hand, bone substitutes used to treat bone loss or defects are classified into autogenous bone, allogeneic bone, xenogeneic bone, and synthetic bone depending on the origin of the material.

Autogenous bone is most preferential but is limited in use because it is difficult for autogenous bone to be obtained in a sufficient amount and it requires repeated surgical procedures. On the other hand, allogeneic bone and xenogeneic bone have limitations in their use due to the risk of disease transmission or immunological rejection.

On the other hand, the synthetic bone graft material may be defined as "artificial synthetic bone that can be used to repair or reconstruct tissue and can be processed with heat or pressure". Since it is cheap and free from size limitation, HA, TCP, etc. are widely used as typical bone substitutes.

Such calcium phosphate-based materials exist in various phases depending on the ratio of calcium to phosphorus (Ca/P ratio). That is, depending on the Ca/P ratio, a material with a Ca/P ratio of 0.5 is monocalcium phosphate monohydrate ($Ca(H_2PO_4)_2 \cdot H_2O$), a material with a Ca/P ratio of 1.0 is dicalcium phosphate dihydrate ($CaHPO_4 \cdot 2H_2O$), a material with a Ca/P ratio of 1.33 is octacalcium phosphate ($Ca_8H_2(PO_4)_6 \cdot 5H_2O$), a material with a Ca/P ratio 1.3 to 1.67 is amorphous calcium phosphate ($Ca_xH_y(PO_4)_z \cdot nH_2O$, n=3 to 4.5, 15% to 20% $H_2O$), a material with a Ca/P ratio 1.5 is α-tricalcium phosphate (α-$Ca_3(PO_4)_2$) or p-tricalcium phosphate (β-$Ca_3(PO_4)_2$), a material with a Ca/P ratio of 1.67 is hydroxy apatite ($Ca_{10}(PO_4)_6(OH)_2$), and a material with a Ca/P ratio of 2.0 is tetracalcium phosphate ($Ca_4(PO_4)_2O$).

On the other hand, the calcium phosphate-based materials have different thermodynamic properties depending on the ratio of calcium and phosphorus and differ in solubility and bone formation in the human body or in a solution that is prepared to mimic the condition of the human body.

Therefore, when different calcium phosphate-based materials are selectively inserted into a body, they show a biological reaction different from the surrounding tissues. It is known that calcium and phosphorus dissolved in a living body greatly affect bone regeneration in the living body.

Furthermore, depending on the preparation method of the calcium phosphate-based material, the calcium phosphate-based material is known to be helpful in cell adhesion or bone regeneration when the material is substituted with monovalent ions such as $Na^+$, $K^+$, $Li^+$, divalent ions such as $Sr^{2+}$, $Ba^{2+}$, $Pb^{2+}$, $Mn^{2+}$, $Sn^{2+}$, $Zn^{2+}$, or trivalent ions such as $Al^{3+}$ or has defects.

Conventional typical synthetic bone substitutes include HA and β-TCP. Depending on the preparation method, such a material is thermally treated at a high temperature of 1000° C. or higher to have a predetermined Ca/P ratio. Alternatively, a portion of phosphate of such a material volatilizes during the thermal treatment to be phase-transitioned into a material with a lower Ca/P ratio.

Therefore, conventional HA and β-TCP are calcium phosphate materials with high crystallinity. When they are inserted into the body, they exhibit a low biodegradation rate and lower bone regeneration compared to octacalcium phosphate (OCP).

Among these synthetic bone graft materials, a synthetic bone comprised of octacalcium phosphate (OCP) has attracted attention as it has been found that when applied to animal experiments, it binds to hard tissue without an inflammatory reaction or formation of new fibrous tissue.

However, although the octacalcium phosphate (OCP) can be produced at room temperature, it is not easy to mass-produce the octacalcium phosphate because it is affected by the temperature and pH of a reaction solution. Therefore, its application is limited due to difficulties in mass production thereof.

In addition, a binder is used to make a bone substitute with a desired shape or form according to the use and purpose of the bone substitute and is prepared from a polymer. Polymers used to prepare the binder are largely categorized into synthetic polymers and natural polymers.

For example, polyethylene, polyester, polyurethane, etc. synthesized from monomers are synthetic polymers. On the other hand, natural polymers are proteins such as collagen, fibrin, and albumin, and polysaccharides such as cellulose, alginate, hyaluronic acid, chitin, etc. and are extracted from animals and plants.

Synthetic polymers have advantages that the mechanical and physical properties thereof can be easily controlled, and they are relatively cheap because their molecular weight can be adjusted during synthesis. However, their biocompatibility is lower than that of natural polymers.

Natural polymers exist abundantly in nature and constitute major components of the human body. However, natural polymers are disadvantageous in that the physical properties thereof cannot be easily controlled compared to synthetic polymers because it is not easy to adjust the molecular weights.

Polymers that can be used as organic binders must meet various requirements such as molecular weight, curing method, etc. Specifically, the polymers must undergo a sterilization process for use in a bone substitute. In the sterilization process, the dose control of electron beam is required. Therefore, when the polymer is inserted into the body, there may be side effects of by-products resulting from decomposition of the polymer in the body, thereby affecting safety.

In addition, since the octacalcium phosphate (OCP) easily converts into a different material depending on the pH, it is difficult to synthesize OCP in large quantities.

SUMMARY

The present invention has been made to solve the above-mentioned problems, and the present disclosure provides a metal inorganic binder that contains octacalcium phosphate and which can be easily mass-produced and is improved in biocompatibility, resorption, and regeneration of new bone, and a method of preparing the inorganic binder.

The objectives of the present disclosure are not limited to the ones described above, and other objectives will be clearly understood by those skilled in the art from the following description.

In order to achieve the above objects, in one embodiment of the present disclosure, there is provided a method of preparing an inorganic binder for medical use, the method including: preparing α-TCP powder and phosphate powder having a predetermined particle size as a starting material; producing a paste having a predetermined viscosity that is suitable for formation of a molded article having a predetermined shape by homogeneously mixing the starting material, adding water or saline to the homogeneously mixed starting material, and kneading the resulting mixture; subjecting the molded article to hydration reaction; and washing and drying the molded article having undergone the hydration reaction to obtain an inorganic binder containing OCP and HA crystal phases.

Preferably, the phosphate powder may be comprised of anyone selected from the group consisting of monobasic sodium phosphate($NaH_2PO_4$) and monobasic potassium phosphate ($KH_2PO_4$).

Preferably, the starting material may be comprised of 78 to 88 wt % of α-TCP powder and 12 to 22 wt % of phosphate powders.

Preferably, in the step of homogeneously mixing the starting material, a planetary mixer rotating at 40 to 60 rpm may be used.

In the step of producing the paste, the homogeneously mixed starting material and the water or saline may be mixed at a ratio of 0.8:1.2.

In the step of producing the paste, the kneading may be performed for 2 to 10 minutes with the use the planetary mixer.

Preferably, in the step of subjecting the molded article to the hydration reaction, the hydration reaction may be performed under conditions of temperature of 70° C. and humidity of 90% or higher for 1 to 2 hours.

Preferably, in the step of washing and drying the molded article having undergone the hydration reaction to obtain the organic binder containing OCP and HA phase, the molded article may be washed one or more times and then dried at temperatures of 40° C. to 60° C.

Preferably, the inorganic binder may contain 80 to 95 wt % of OCP and 5 to 20 wt % of HA.

In the method of preparing bone substitution materials using the medical inorganic binder according to one embodiment of the present disclosure, the starting material may further contain one or more kinds of powder selected from the group consisting of HA, β-TCP, OCP, and DCPD powders.

Preferably, the additional powder may be added in an amount of 0.1 to 31 wt % with respect to the total weight of the α-TCP powder.

Preferably, the starting material may further contain metal ions and a buffering agent.

Preferably, the metal ions may be $Zn^{2+}$, $K^+$, or $Mg^{2+}$, and the buffering agent may be dibasic sodium phosphate ($Na_2HPO_4$) or dibasic potassium phosphate ($K_2HPO_4$).

Preferably, a pH adjuster may be further added to control the acidity that changes due to the addition of the metal ions, and the pH adjuster may be acetic acid ($CH_3COOH$).

Preferably, the inorganic binder may have a pH of 5.0 to 6.0.

The inorganic binder and bone substitute prepared by the methods according to embodiments of the present disclosure can be easily mass-produced and are improved in terms of biosafety, resorption, and bone regeneration capability.

BRIEF DESCRIPTION OF THE DRAWINGS

The above and other objectives, features, and other advantages of the present invention will be more clearly understood from the following detailed description taken in conjunction with the accompanying drawings, in which.

DETAILED DESCRIPTION

As the terms used to describe the present invention in the present disclosure, as many general terms as possible are selected. However, in certain cases, terms that are chosen by the inventors of the present invention may be used. In such cases, the meanings of the terms should be understood not simply by the name but by the detailed description of the invention.

Hereinafter, the technical aspects of the present invention will be described in detail with reference to the preferred embodiments illustrated in the accompanying drawings.

Figure 1:
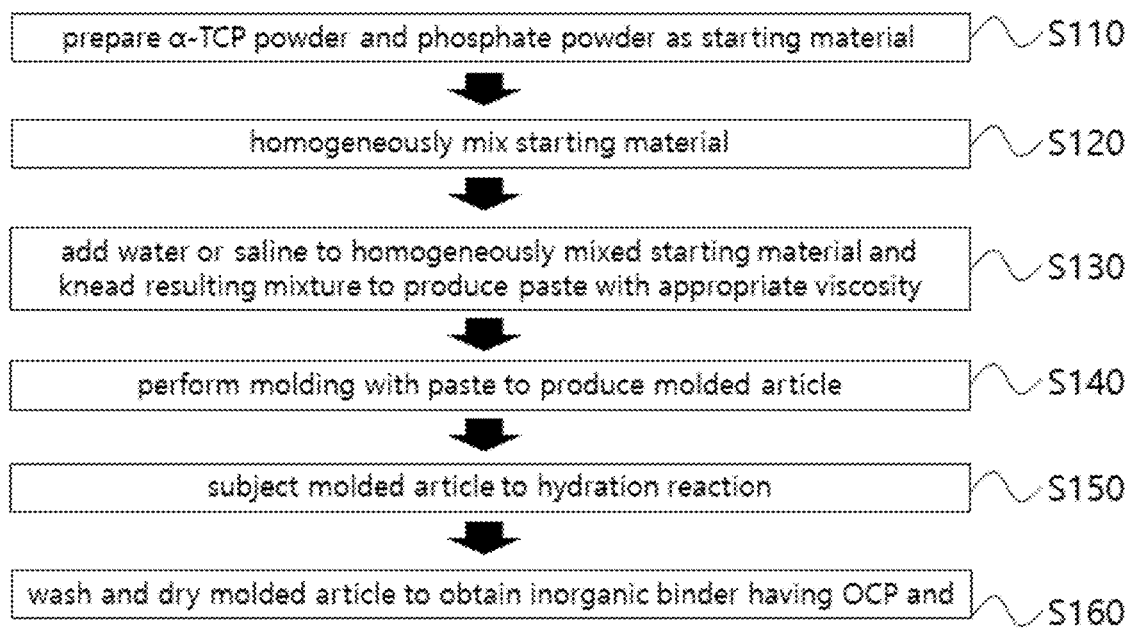
FIG. 1 is an overall process flowchart illustrating a method of preparing a medical inorganic binder according to one embodiment of the present disclosure.
Figure 2:
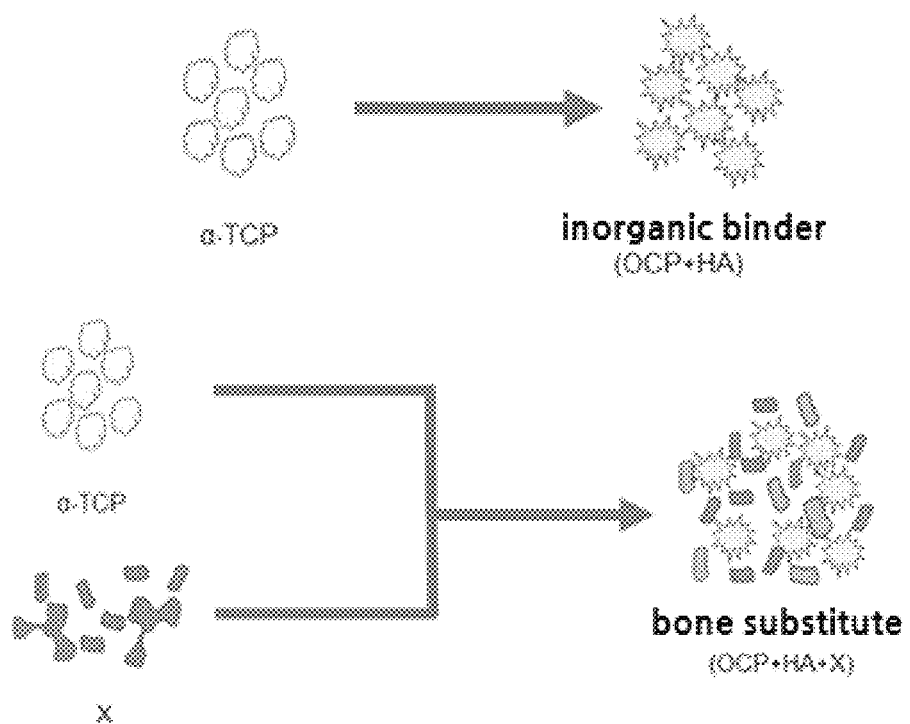
FIG. 2 is a schematic view illustrating a method of preparing a medical inorganic binder and a method of preparing a bone substitute, according to embodiments of the present disclosure.
Figure 3:
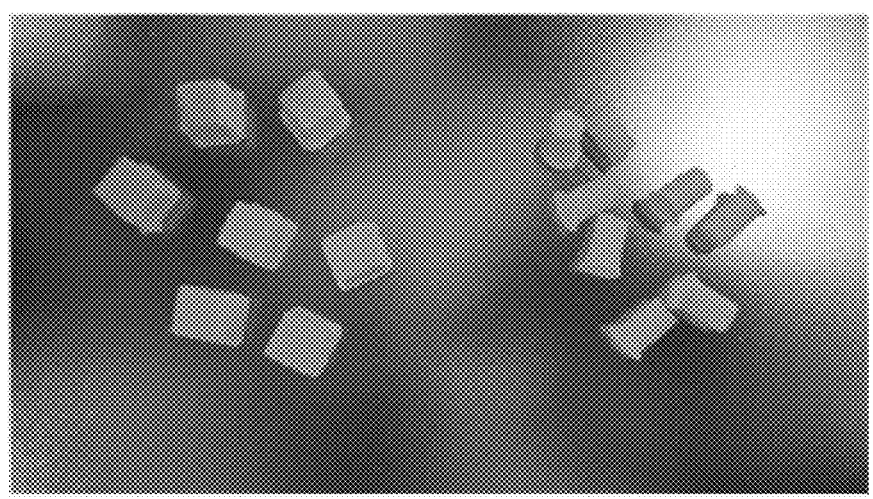
FIG. 3 is an image of a molded article made from the inorganic binder prepared by the method according to one embodiment of the present disclosure.

FIG. 1 is an overall process flowchart illustrating a method of preparing a medical inorganic binder according to one embodiment of the present disclosure. FIG. 2 is a schematic view illustrating a medical inorganic binder according to one embodiment of the present disclosure and a method of preparing a bone substitute using the medical inorganic binder. FIG. 3 is an image of a molded product made from the inorganic binder according to one embodiment of the present disclosure.

Referring to FIGS. 1 to 3, the medical inorganic binder preparation method according to one embodiment of the present disclosure includes step S110 of preparing α-TCP powder and phosphate powder that have a predetermined particle size to obtain a starting material.

The particle size of the α-TCP powder is 106 µm or smaller.

In the embodiment of the present disclosure, the phosphate powder is comprised of monobasic sodium phosphate ($NaH_2PO_4$), monobasic potassium phosphate ($KH_2PO_4$), or a combination thereof.

The phosphate powder is used as an additive for a hydration reaction. More specifically, the phosphate powder is used for curing by undergoing acid-base reaction and hydration reaction with calcium ions.

In the embodiment of the present disclosure, preferably, the starting material includes 78 to 88 wt % of α-TCP powder and 12 to 22 wt % of phosphate powder. More preferably, the starting material includes 84 wt % of α-TCP and 16 wt % of phosphate powders.

The medical inorganic binder preparation method according to one embodiment of the present disclosure includes step S120 of homogeneously mixing the starting material.

The homogeneous mixing S120 is performed using a planetary mixer. In this step, the planetary mixer is rotated at 40 to 60 rpm.

However, since the specified rotational speed is determined to mix the powder evenly, the impact of rotation speed on the inorganic binder preparation is not significant.

The medical inorganic binder preparation method according to one embodiment of the present disclosure includes step S130 of producing a paste with a predetermined viscosity after adding water or saline to the homogeneous starting material.

The viscosity of the paste depends on the amount of distilled water or saline that is added to the starting material. In the embodiment of the present disclosure, in step S130, the homogeneous starting material and water or saline are mixed at a ratio of 0.8:1.2 or alternatively a ratio of 1:1.

In the paste preparation step S130, the mixture is kneaded for 2 to 10 minutes using a planetary mixer.

The specific time duration range is determined for the reason that although acid-base reaction progresses during the kneading so that the mixture is imparted with properties required for a binder, it is preferable that the maximum value time duration is not loner than 10 minutes to increase the content of octacalcium phosphate.

When the working time duration is longer than 10 minutes, the content of HA increases with the progress of hydration reaction but the octacalcium phosphate experiences phase transition into a different calcium phosphate. Therefore, the time duration for the kneading is determined to in the range described above.

The medical inorganic binder preparation method according to one embodiment of the present disclosure includes step S140 of forming a molded article by molding the paste into a predetermined shape.

There is no special limitation to the shape of the molded article because the molded article comes in various shapes depending on the shape of a mold. However, the paste is required to have a suitable viscosity to fill the mold.

The molded article according to one embodiment of the present disclosure can be uses as a bone substitute. In the case where the final product is amorphous granule, a mold is not needed. The paste is simply ground to be used as a bone substitute.

The medical inorganic binder preparation method according to one embodiment of the present disclosure includes step S150 of subjecting the molded article to hydration reaction.

The hydration reaction step S150 of the molded article is performed under conditions of 70° C. and 90% or higher of humidity for 1 to 2 hours. More preferably, the hydration reaction step S150 may be performed for 1.5 hours.

However, as described above, the reason for limiting the duration of the hydration reaction (i.e., duration of iso-thermal and iso-humidity control) is that the phase change occurs from α-TCP to octacalcium phosphate depending on the duration of the iso-thermal and iso-humidity control.

More specifically, a short duration of iso-thermal and iso-humidity control leads to a reduced hydration reaction rate so that α-TCP may unintentionally remain. On the other hand, when the iso-thermal and iso-humidity control is maintained for over two hours, the octacalcium phosphate undergoes a phase change into HA, resulting in an issue such as increased HA content or the creation of other types of non-intended calcium phosphates. Therefore, the duration of the iso-thermal and iso-humidity control is limited to the range described above.

In addition, the medical inorganic binder preparation method according to one embodiment of the present disclosure includes step S160 of washing and drying the molded article having undergone hydration reaction to obtain an inorganic binder containing OCP and HA crystalline phases.

In the washing and drying step S160, the molded article is primarily dried at temperatures of 40° C. to 60° C. to remove water remaining in the obtained inorganic binder, is then washed with water to remove residual by-products, and is secondarily dried at temperatures of 40° C. to 60°.

On the other hand, since the washing may be performed one or more times as necessary, so no special limitation shall be placed on the number of times of the washing.

The inorganic binder prepared by the medical inorganic binder preparation method according to one embodiment of the present disclosure contains 80 to 95 wt % of OCP and 5 to 20 wt % of HA.

Hereinafter, a method of preparing a bone substitute using the medical inorganic binder according to one embodiment of the present disclosure will be described in detail.

In the bone substitute preparation method according to one embodiment of the present disclosure, the starting material additionally includes at least one selected from the group consisting of HA, β-TCP, OCP, and DCPD powders.

In the embodiment of the present disclosure, the additional powder is added in an amount of 0.1 to 31 wt % with respect to the total weight of the α-TCP.

On the other hand, the additional powders may be selected to be used for bone substitutes having different shapes and forms depending on the bone replacement site.

In more detail, HA powder is used for bone replacement sites where strength and bone repair scaffolds are important. OCP or β-TCP powder may be added when scaffolds and bone regeneration are required. More preferably, the additional powders can be used in combination for bone regeneration and enhancement of bone strength.

In the bone substitute preparation method using the medical inorganic binder according to one embodiment of the present disclosure, metal ions and a buffer are added to the starting material. In this case, the metals ions are $Zn^{2+}$, $K^+$, or $Mg^{2+}$ ions, and the buffer is dibasic sodium phosphate ($Na_2HPO_4$) or dibasic potassium phosphate ($K_2HPO_4$).

The buffer is optionally used depending on the amount of the additional powder added to adjust the acidity or to control the reaction rate.

In more detail, the phosphate powder undergoes acid-base reaction or hydration reaction with the calcium ions of α-TCP as described above, thereby functioning as a curing agent. The buffer functions to reduce the speed of the hydration reaction.

Phosphate exhibits a pH of 4.2 to 4.6 in an aqueous solution. Especially, monobasic potassium phosphate is an acid exhibiting a pH of 4.4 to 4.9 and causes phase changes of α-TCP into OCP and HA through the curing caused by the acid-base reaction and the hydration reaction.

The speed control of the phase change described above can be obtained by adjusting the acidity. For the acidity control during the acid dissociation of hydrogen ions and the hydrolysis dehydration, dibasic sodium phosphate having a pH of 9.0 to 9.6 or dibasic potassium phosphate having a pH of 8.7 to 9.3 is used as an alkali substance.

Meanwhile, tribasic sodium phosphate ($Na_3PO_4$) and tribasic potassium phosphate ($K_3PO_4$) are not used as an acidity adjuster because they are alkali substances having a pH of pH 11.5 to 12.5.

In the bone substitute preparation method using the medical inorganic binder according to one embodiment of the present disclosure, the adjustment of acidity is required during the kneading.

Monobasic sodium phosphate that is a phosphate powder is used so that a pH of 5.0 to 6.0 can be maintained. When metal ions such as zinc are added, ZnO (pH 6 to 7), $K_2CO_3$ (pH 11 to 12), or MgO (pH 8 to 10) may be selected. These substances are used as alkaline materials.

Depending on the preparation method of the calcium phosphate-based material, the calcium phosphate-based material is helpful in cell adhesion or bone regeneration when the calcium phosphate-based material is substituted with monovalent ions such as Nat, $K^+$, $Li^+$, divalent ions such as $Sr^{2+}$, $Ba^{2+}$, $Pb^{2+}$, $Mn^{2+}$, $Sn^{2+}$, $Zn^{2+}$, or trivalent ions such as $Al^{3+}$ or has defects.

On the other hand, the buffer is used when the acid-base reaction or hydration reaction of the phosphate powder takes place fast.

However, when an alkali substance is used to add metal ions, a change in acidity occurs during the kneading. Therefore, in the embodiment of the present disclosure, acetic acid ($CH_3COOH$) that can be easily ionized in an aqueous solution is used as an additional pH adjuster to prevent alkalization that occurs due to metal ions during the acid-base reaction at the early stage, so that the solution can be adjusted to be in a weak acid state.

However, because weak acids or weak bases exist in an ionized molecular state in water, when metal elements are added before the addition of acetic acid and then the acidity of the solution is controlled using acetic acid, the inorganic binder can be adjusted to be in a pH range of 5.0 to 6.0 by the acid-base reaction.

Hereinafter, the effects of the medical inorganic binder and the bone substitute according to embodiments of the present disclosure will be described in detail.

Figure 4:
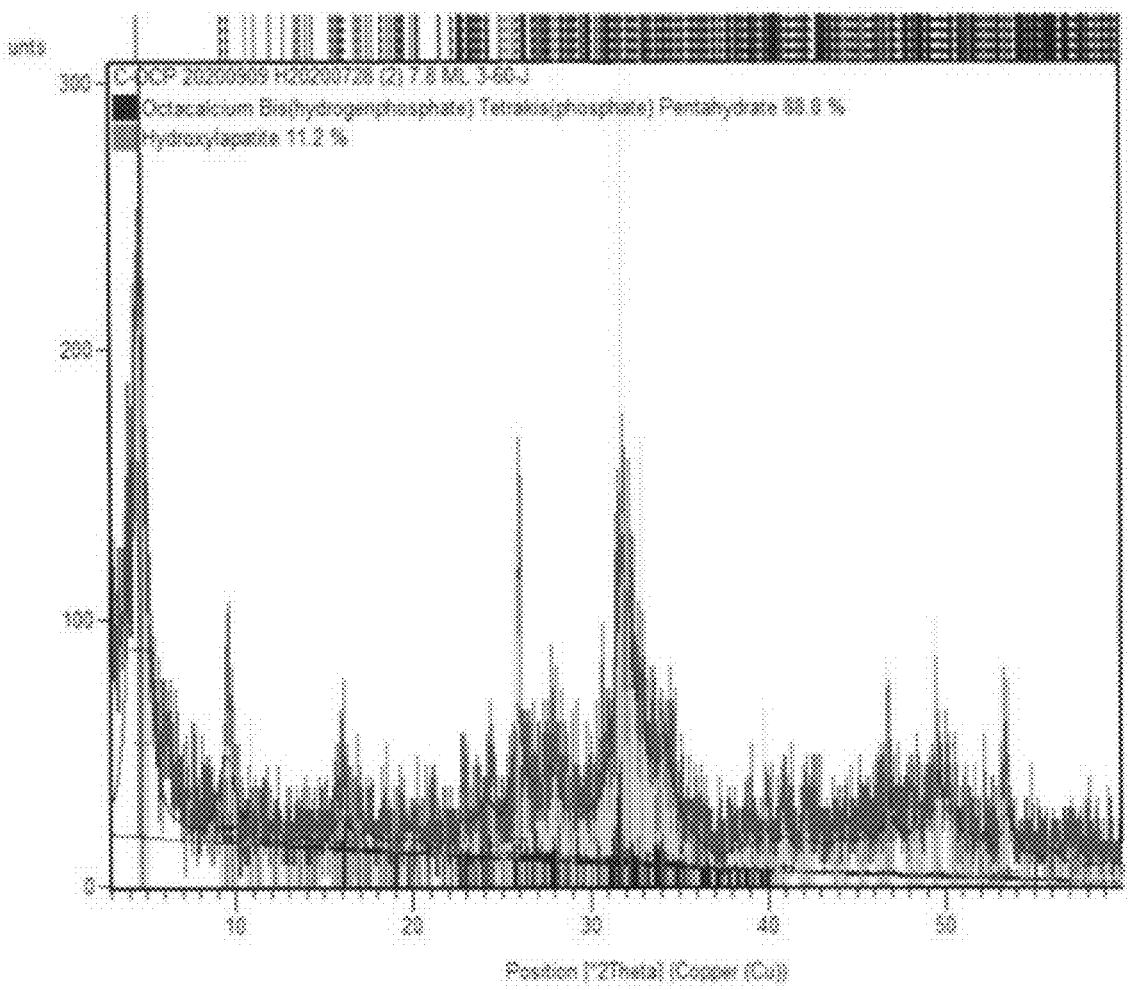
FIG. 4 is the result of XRD analysis of the inorganic binder prepared by the method of FIG. 1.
Figure 5:
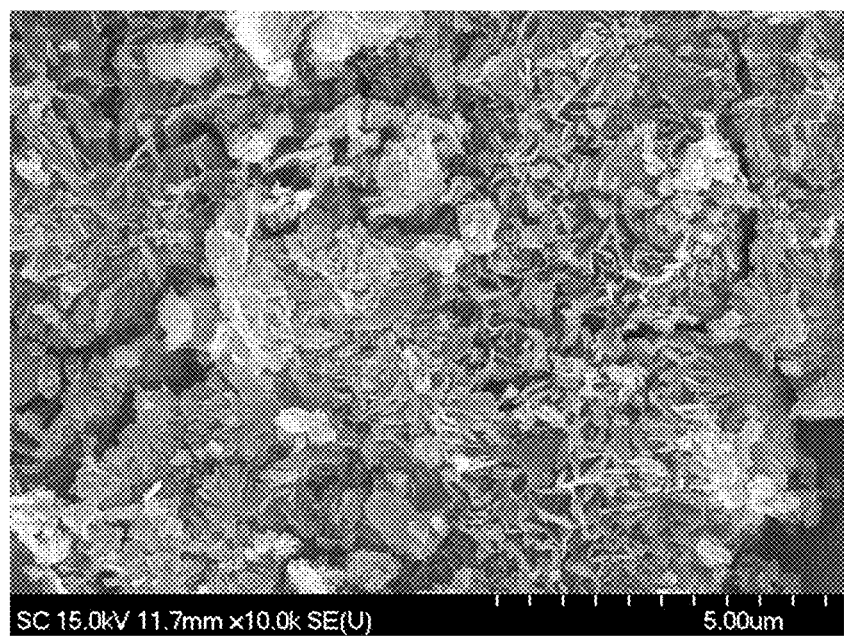
FIG. 5 is an image showing the surface morphology of the inorganic binder.
Figure 6:
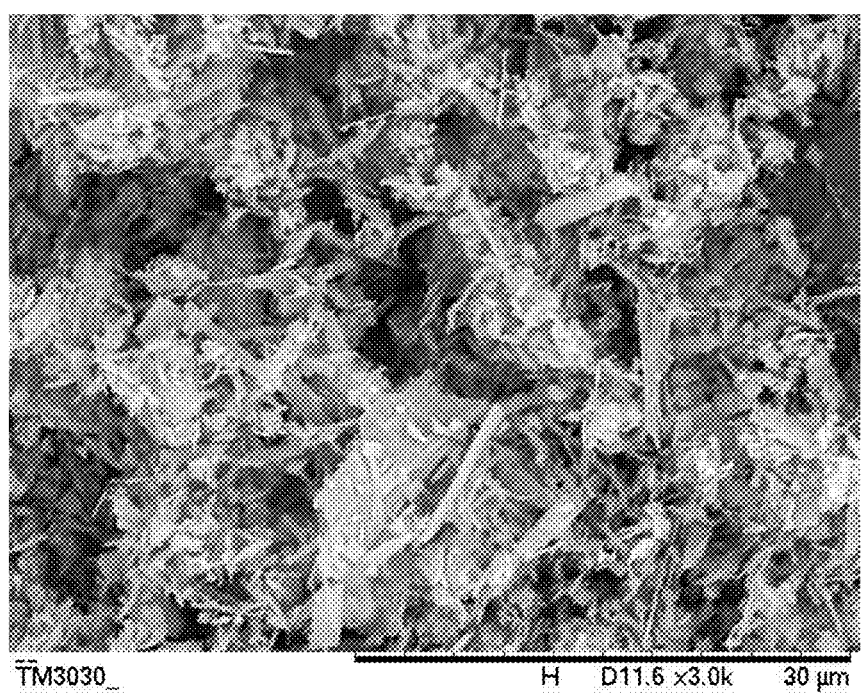
FIG. 6 is an image of a bone substitute made from the medical inorganic binder by using the preparation method according to one embodiment of the present disclosure.
Figure 7:
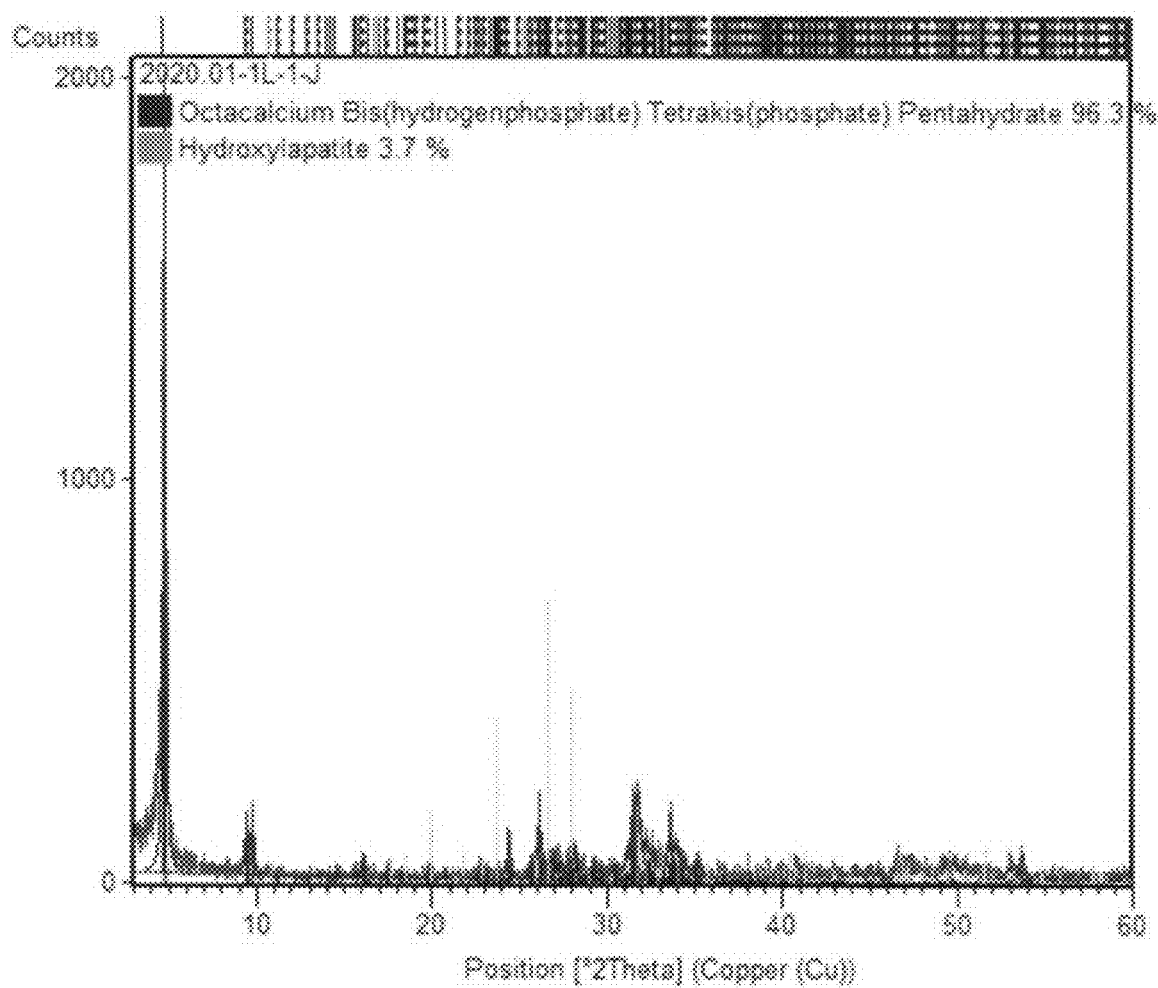
FIG. 7 is the result of XRD analysis of the bone substitute.

FIG. 4 is the result of the XRD analysis of the inorganic binder prepared according to the method of FIG. 1, FIG. 5 is an image of the surface morphology of the inorganic binder, FIG. 6 is an image of the bone substitute prepared using the bone substitute preparation method using the medical inorganic binder according to one embodiment of the embodiment of the present disclosure, and FIG. 7 is the result of the XRD analysis of the bone substitute.

Referring to FIGS. 4 to 7, the medical inorganic binder according to one embodiment of the present disclosure and the bone substitution using the medical inorganic binder are found to include octacalcium phosphate and an HA crystalline phase, and to have a slightly roughened surface due to the acid-base reaction and the hydration reaction.

The medical inorganic binder prepared by the method according to the embodiment of the present disclosure and the bone substitute including the same were assessed for their biocompatibility by Korea Testing & Research Institute (KTRI).

For assessment of the biological safety, tests for intracutaneous reactivity, acute dermal toxicity, and genotoxicity (chromosomal aberration and reverse mutation) were conducted.

1. Intracutaneous Reactivity Test

To evaluate the intracutaneous reactivity of a test substance, three rabbits were intradermally injected, and local responses were observed in a brief time, 24 hours, 48 hours, and 72 hours after the injection. The following results were obtained:

during the test, no death (or moribund) and general symptoms were observed during the injection of the test substance;

during the test, no weight changes were observed due to the injection of the test substance;

in a brief time, 24 hours, 48 hours, and 72 hours after the injection, local responses (irritation) were examined, revealing no erythema and crusts at the injection sites of a control material and the test substance;

little swelling was observed at some injection sites of the test substance in all individuals, but given the appearance of the test substance, the swelling was considered as white particles attributable to the effusion of the test substance rather than edema caused by fluid retention;

the difference between the test results of the test substance and the control material for elute was calculated as "0.20" for sterile physiological saline elute and "0.20" for cottonseed oil elute.

Based on the test results in which the difference of the elute of a calcium phosphate compound between the test substance and the control material was less than 1.0 when the test was performed on rabbits, the test substance was proven to meet the requirement for intracutaneous reactivity.

2. Acute Dermal Toxicity Test

To perform an acute transcutaneous toxicity test for calcium phosphate compounds, a test substance was injected once into Sprague Dawley® (SD®) rats (female) through dermal administration at doses 200, 1000, and 2000 mg/kg B.W. (for range-finding study) and 2000 mg/kg B.W. (for main study).

Mortality, general symptoms, and weight changes of the rats had been observed for 14 days after the test substance was administered, and the rats were sacrificed and visually examined for abnormalities in the organ by autopsy.

The results revealed:

no dead animals were found during the test due to the administration of the test substance;

as to observation of general symptoms, redness was observed at 1000 mg/kg B.W. (for range-finding study).

weight measurements showed no weight change attributable to the administration of the test substance; and autopsy findings did not show any abnormalities in all administration groups.

The acute dermal toxicity test was conducted in accordance with the OECD Guideline for testing of chemicals, Section 4, TG402. As a result, the test substance was proven to be biologically safe and compatible as being classified as Category 5/Unclassified according to the standard "The Globally Harmonized System of Classification and Labelling of Chemicals (GHS)" that is globally accepted.

3. Genotoxicity Test

Genotoxicity tests were divided into a chromosomal aberration test and a reverse mutation test.

First, a chromosomal aberration test was conducted using Chinese hamster-derived lung cells (CHL) to evaluate whether calcium phosphate compounds induce chromosomal aberrations. The test was carried out according to OECD Guideline for Testing of Chemicals, No. 473 473.

A concentration determination test was conducted for concentrations of 62.5, 125, 250, 500, 1000, and 2000 μg/mL by a short-term treatment method in the absence of S9 mix (hereinafter, referred to as "−S9") and in the presence of S9 mix (hereinafter, referred to as "+9") and by a 24-hour continuous treatment method (hereinafter, referred to as 24-hour treatment).

As a result of the test, when cytotoxicity was calculated using relative increase in cell counts (RICC) for the −S9 mix group, the +S9 mix group, and the 24-hour treatment group, the concentrations of the test sample at which the cytotoxicity (RICC) was 55% are summarized as follows:

| | Cell growth index (RICC %) | | |
|---|---|---|---|
| | Short-term treatment test | | Continuous treatment test |
| | −S9 mix | +S9 mix | 24-hour exposure |
| RICC$_{55}$ | 50.1 μg/mL | 91.2 μg/mL | 25.1 μg/mL |

Based on the results of the concentration determination test, the concentrations of the test substance applied to the respective treatment groups were set as described below, and the chromosomal aberration test was performed for each treatment group.

| Experimental Conditions | S9 mix | Concentration (μg/mL) |
|---|---|---|
| Chromosomal aberration test (short-term treatment) | − | 20, 40, 80, 90, 100 |
| | + | 77.5, 155, 310, 330, 350 |
| Chromosomal aberration test (continuous treatment) | − | 17.5, 35, 70, 80, 90 |

Based on the results of the chromosomal aberration test, slide observation was performed on samples except for samples with concentrations exhibiting RICC 60% or higher. The slides observed are as follows:

| Experimental Conditions | S9 mix | Concentration (μg/mL) |
|---|---|---|
| Chromosomal aberration test (short-term treatment) | − | 20, 40, 80, 90, 100 |
| | + | 77.5, 155, 310, 330, 350 |
| Chromosomal aberration test (continuous treatment) | − | 17.5, 35, 70, 80, 350 |

Slide observations showed that the frequency of chromosomal abnormalities was less than 5% for both the structural and numerical abnormalities. Therefore, the test substance was not determined (i.e., negative response) to cause chromosomal abnormalities on CHL/IU cells.

On the other hand, the reversion mutation test was carried out according to OECD Guideline for testing of chemicals, Section 4, TG. No. 471.

More specifically, to evaluate whether the test substance (calcium phosphate compound) induces bacterial reverse mutation, the test was conducted using four Salmonella typhimurium strains (TA98, TA100, TA1535 and TA1537) which are histidine-demanding strains and an Escherichia coli which is a tryptophan-demanding strain.

The test was conducted by the pre-incubation method in the presence of a metabolic activation system (+S9 mix) and in the absence of a metabolic activation system (−S9 mix).

The concentration determination test was conducted for 50, 150, 500, 1500 and 5000 μg/plate. As a result, it was not confirmed that strain growth was inhibited by the toxicity of the test substance in the absence of S9 mix (−S9 mix) and in the presence of S9 mix (+S9 mix).

It was confirmed that precipitation of the test substance occurred at concentrations of over 150 pg/plate with or without the use of the metabolic activation system.

The group treated with the test substance did not show a significant increase in the number of revertant colonies, compared to the negative control.

Given the results, the test was conducted, without a metabolic active system (−S9 mix) and with a metabolic activation system (+S9 mix), at concentrations of 313, 625, 1250, 2500, 5000 μg/plate (using TA98, TA100, TA1535, TA1537, and WP2 uvr A).

As a result, it was not confirmed that without S9 mix (−S9 mix) and with S9 mix (+S9 mix), strain growth was inhibited by the toxicity of the test substance.

It was confirmed that precipitation of the test substance occurred at concentrations of over 313 pg/plate with or without the use of the metabolic activation system.

The group treated with the test substance did not show a significant increase in the number of revertant colonies, compared to the negative control.

The negative and positive control values for this test were within an appropriate range of a test study facility.

The number of revertant colonies caused by the positive control increased to be more than twice the number of revertant colonies caused by the negative control for all experimental strains in the absence of a metabolic activation system (−S9 mix) and in the presence of a metabolic activation system (+S9 mix).

Based on the test results, it was determined that the test substance did not have mutagenicity.

In addition, as a test for the formation of new bone by the inorganic binder according to one embodiment of the present disclosure, a RANKL/ALP test was conducted to compare the activity of osteoclasts and that of osteoblasts.

The inorganic binder according to one embodiment of the present disclosure was used as a test group, and commercially available BCP (HA and β-TCP=2:8) was used a control group.

MG63 was used as cells. As a result, the activity of osteoclasts slightly decreased with time by the control group and was inferior to the control group. On the other hand, the activity of osteoblasts participating in formation of new bone increased with time and was superior to the control group.

Based on the results that the activity of osteoclasts is slightly inhibited, and the activity of osteoblasts is promoted, the inorganic binder according to one embodiment of the present disclosure was confirmed to be useful as a bone substitute.

TABLE 1

MG63 cell activity (RANKL)

| Sample | 7 days | 14 days |
|---|---|---|
| Test group | 11.32 | 23.44 |
| Control group | 14.13 | 28.55 |

TABLE 2

MG63 cell activity (ALP)

| Sample | 7 days | 14 days |
|---|---|---|
| Test group | 17.92 | 22.38 |
| Control group | 9.22 | 13.90 |

Figure 8:
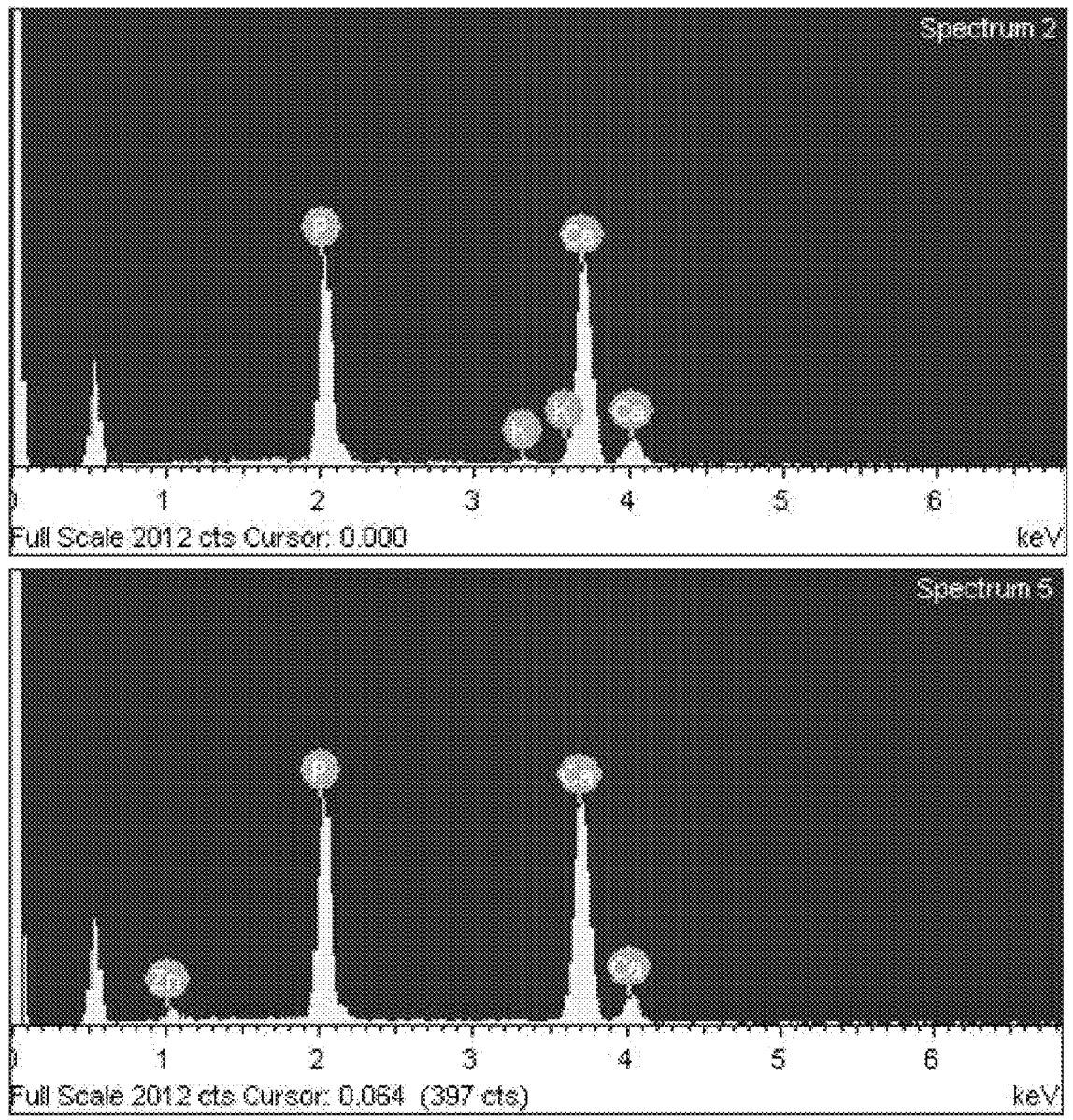
FIG. 8 is a graphical representation showing the basis of the calculation of the detection quantity shown in Table 3.

Table 3 and FIG. 8 show changes in detection and content of metal ions released from the metal-added inorganic binder according to one embodiment of the present disclosure. From the test results, it is found that metal ions are detected from the inorganic binder according to one embodiment of the present disclosure.

TABLE 3

|  | Ca | P | K or Zn | Total |
|---|---|---|---|---|
| K | 59.994 | 39.996 | 0.01 | 100 |
|  | 57 | 38 | 5.00 | 100 |
| Zn | 59.994 | 39.996 | 0.01 | 100 |
|  | 57 | 38 | 5.00 | 100 |

Consequently, the inorganic binder for medical use according to one embodiment of the present disclosure and the bone substitute preparation method using the inorganic binder have the advantage that the inorganic binder and the bone substitute can be easily and rapidly manufactured in various shapes and forms because OCP is included and calcium phosphates including α-TCP are added. In addition, since the reaction process of raw materials can be controlled during the manufacture, the fraction of the crystalline phase in the bone substitute can be controlled, and thus the bone substitute has good adhesion, biocompatibility, resorption, and bone regeneration.

In addition, the medical inorganic binder and the bone substitute preparation method according to embodiments of the present disclosure have the advantage that the inorganic binder can be prepared without a high-temperature calculation process.

Although the present invention has been described with reference to the preferred example, those ordinarily skilled in the art will appreciate that the present invention is not limited to the example described above and can be diversely changed and modified without departing from the scope of the spirit of the present invention.

What is claimed is:

1. A method of preparing an inorganic binder for medical use, the method comprising:
preparing a starting material using α-tricalcium phosphate (α-TCP) powder and phosphate powder each of which has a predetermined particle size;
homogeneously mixing the starting material;
producing a paste having a predetermined viscosity that is suitable for preparation of a molded article by adding water or saline to the homogeneously mixed starting material and kneading the paste;
molding the paste into a predetermined shape to obtain the molded article;
subjecting the molded article to hydration reaction; and
washing and drying the molded article having undergone the hydration reaction to obtain the inorganic binder containing octacalcium phosphate (OCP) and hydroxy apatite (HA) crystalline phases,
wherein the phosphate powder comprises monobasic sodium phosphate($NaH_2PO_4$), monobasic potassium phosphate ($KH_2PO_4$), or a combination thereof.

2. The method according to claim 1, wherein the starting material comprises 78 to 88 wt % of a-TCP powder and 12 to 22 wt % of phosphate powders.

3. The method according to claim 2, wherein, in the homogeneous mixing of the starting material, a planetary mixer is used to rotate at 40 to 60 rpm.

4. The method according to claim 3, wherein in the producing of the paste, the homogeneously mixed starting material and the water or saline are mixed at a ratio of 0.8:1.2.

5. The method according to claim 4, wherein in the producing the paste, the kneading is performed for 2 to 10 minutes using a planetary mixer.

6. The method according to claim 5, wherein in the subjecting of the molded article to the hydration reaction, the hydration reaction is performed under conditions of temperature of 70° C. and humidity of 90% or higher for 1 to 2 hours.

7. The method according to claim 6, wherein in the washing and drying of the molded article having undergone the hydration reaction, the molded article is washed one or more times and then dried at temperatures of 40° C. to 60° C.

8. The method according to claim 7, wherein the inorganic binder comprises 80 to 95 wt % of the OCP and 5 to 20 wt % of the HA.

9. The method according to claim 1, wherein the starting material further comprises one or more additional powders selected from the group consisting of HA, β-TCP, OCP, and dicalcium phosphate dihydrate (DCPD) powders.

10. The method according to claim 9, wherein the additional powders are contained in an amount of 0.1 to 31 wt % with respect to a total weight of the α-TCP powder.

11. The method according to claim 10, wherein the starting material further comprises metal ions and a buffering agent.

12. The method according to claim 11, wherein the metal ions comprise $Zn^{2+}$, $K^+$, or $Mg^{2+}$, and the buffering agent comprises dibasic sodium phosphate ($Na_2HPO_4$) or dibasic potassium phosphate ($K_2HPO_4$).

13. The method according to claim 12, wherein a pH adjuster is added to control an acidity of the starting material due to addition of the metal ions, and the pH adjuster is acetic acid ($CH_3COOH$).

14. The method according to claim 13, wherein the inorganic binder has a pH of 5.0 to 6.0.

* * * * *